(12) United States Patent
Bailey

(10) Patent No.: US 9,992,987 B2
(45) Date of Patent: *Jun. 12, 2018

(54) FISHING DATA SHARING AND DISPLAY

(71) Applicant: Navico Holding AS, Egersund (NO)

(72) Inventor: Paul Robert Bailey, Auckland (NZ)

(73) Assignee: NAVICO HOLDING AS, Egersund (NO)

( * ) Notice: Subject to any disclaimer, the term of this patent is extended or adjusted under 35 U.S.C. 154(b) by 442 days.

This patent is subject to a terminal disclaimer.

(21) Appl. No.: 14/280,373

(22) Filed: May 16, 2014

(65) Prior Publication Data

US 2015/0058237 A1    Feb. 26, 2015

Related U.S. Application Data

(60) Provisional application No. 61/868,444, filed on Aug. 21, 2013.

(51) Int. Cl.
*G06Q 30/02* (2012.01)
*G06Q 10/10* (2012.01)
(Continued)

(52) U.S. Cl.
CPC ............... *A01K 97/00* (2013.01); *A01K 79/00* (2013.01); *A01K 99/00* (2013.01); *A61B 5/1118* (2013.01); *A61B 5/1123* (2013.01); *G01B 21/00* (2013.01); *G01C 21/20* (2013.01); *G01C 21/203* (2013.01); *G06F 3/014* (2013.01); *G06F 3/017* (2013.01); *G06F 3/0231* (2013.01); *G06F 3/0346* (2013.01); *G06F 11/3438* (2013.01); *G06F 11/3476* (2013.01); *G06F 15/0225* (2013.01); *G06F 17/30867* (2013.01);
(Continued)

(58) Field of Classification Search
CPC ........ A01K 97/00; A01K 79/00; A01K 99/00; G06Q 50/01
USPC .................................................. 705/1.1–912
See application file for complete search history.

(56) References Cited

U.S. PATENT DOCUMENTS 4,751,787 A    6/1988   Jonsson
4,829,493 A    5/1989   Bailey
(Continued)

FOREIGN PATENT DOCUMENTS

DE    102004059619 A1    6/2006
EP        749687 A1    12/1996
(Continued)

OTHER PUBLICATIONS

PCT International Search Report and Written Opinion; PCT/IB2014/063979; dated Jan. 7, 2015.
(Continued)

*Primary Examiner* — Jonathan P Ouellette
(74) *Attorney, Agent, or Firm* — Nelson Mullins Riley & Scarborough LLP

(57) ABSTRACT

Various implementations described herein are directed to a non-transitory computer readable medium having stored thereon computer-executable instructions which, when executed by a computer, may cause the computer to automatically receiving fishing data recorded during a fishing trip. The computer may receive a selection of a first group of subscribers that can access the fishing data. The computer may grant permissions to the first group of subscribers to access the fishing data.

20 Claims, 10 Drawing Sheets

(51) Int. Cl.
| | |
|---|---|
| *G06Q 10/06* | (2012.01) |
| *G06Q 30/06* | (2012.01) |
| *G06Q 99/00* | (2006.01) |
| *A01K 97/00* | (2006.01) |
| *H04N 5/232* | (2006.01) |
| *H04N 5/91* | (2006.01) |
| *H04N 21/4335* | (2011.01) |
| *G08C 17/02* | (2006.01) |
| *G06F 3/01* | (2006.01) |
| *G06F 3/023* | (2006.01) |
| *G06F 15/02* | (2006.01) |
| *G06T 11/20* | (2006.01) |
| *G06T 7/60* | (2017.01) |
| *G11B 27/031* | (2006.01) |
| *G11B 27/17* | (2006.01) |
| *G11B 31/00* | (2006.01) |
| *A01K 99/00* | (2006.01) |
| *G01C 21/20* | (2006.01) |
| *A61B 5/11* | (2006.01) |
| *G01B 21/00* | (2006.01) |
| *G06Q 10/00* | (2012.01) |
| *G06Q 50/00* | (2012.01) |
| *G06F 17/30* | (2006.01) |
| *A01K 79/00* | (2006.01) |
| *G06F 11/34* | (2006.01) |
| *G06K 9/00* | (2006.01) |
| *G11B 27/28* | (2006.01) |
| *G11B 27/34* | (2006.01) |
| *G06F 3/0346* | (2013.01) |
| *H04Q 9/00* | (2006.01) |
| *G06T 7/246* | (2017.01) |
| *G06T 7/292* | (2017.01) |
| *B63B 49/00* | (2006.01) |
| *G01S 15/96* | (2006.01) |
| *G06F 11/30* | (2006.01) |
| *G01S 7/00* | (2006.01) |

(52) U.S. Cl.
CPC ......... *G06K 9/00342* (2013.01); *G06Q 10/00* (2013.01); *G06Q 50/01* (2013.01); *G06T 7/246* (2017.01); *G06T 7/292* (2017.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04N 5/232* (2013.01); *H04N 5/91* (2013.01); *H04N 21/4335* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01); *G06T 2207/30196* (2013.01); *G08C 2201/32* (2013.01); *H04Q 2209/43* (2013.01); *Y02B 60/165* (2013.01); *Y02D 10/34* (2018.01)

(56) References Cited

U.S. PATENT DOCUMENTS

| | | |
|---|---|---|
| 4,879,697 A | 11/1989 | Lowrance et al. |
| 5,025,423 A | 6/1991 | Earp |
| 5,191,341 A | 3/1993 | Gouard et al. |
| 5,228,228 A | 7/1993 | Meissner |
| 5,321,391 A | 6/1994 | Fox |
| 5,446,775 A | 8/1995 | Wright et al. |
| 5,537,380 A | 7/1996 | Sprankle, Jr. et al. |
| 5,546,695 A | 8/1996 | Langer |
| 6,045,076 A * | 4/2000 | Daniels ............ A01K 89/01555 188/268 |
| 6,125,571 A | 10/2000 | Sigwald |
| 6,222,449 B1 | 4/2001 | Twining |
| 6,225,984 B1 | 5/2001 | Crawford |
| 6,252,544 B1 | 6/2001 | Hoffberg |
| 6,263,147 B1 | 7/2001 | Tognazzini |
| 6,321,158 B1 | 11/2001 | DeLorme et al. |
| 6,411,283 B1 | 6/2002 | Murphy |
| 6,418,080 B2 | 7/2002 | Inouchi |
| 6,421,299 B1 | 7/2002 | Betts et al. |
| 6,459,372 B1 | 10/2002 | Branham et al. |
| 6,567,792 B1 | 5/2003 | Arnold |
| 6,584,722 B1 | 7/2003 | Walls et al. |
| 6,587,740 B2 | 7/2003 | Byrne et al. |
| 6,751,626 B2 | 6/2004 | Brown et al. |
| 6,761,692 B2 | 7/2004 | Angelsen et al. |
| 6,798,378 B1 | 9/2004 | Walters |
| 6,816,782 B1 | 11/2004 | Walters et al. |
| 7,002,579 B2 | 2/2006 | Olson |
| 7,236,426 B2 | 6/2007 | Turner et al. |
| 7,243,457 B1 | 7/2007 | Smith et al. |
| 7,319,992 B2 * | 1/2008 | Gaos .................. G06Q 30/02 348/E7.05 |
| 7,321,824 B1 | 1/2008 | Nesbitt |
| 7,430,461 B1 | 9/2008 | Michaels |
| 7,652,952 B2 | 1/2010 | Betts et al. |
| 7,669,360 B2 | 3/2010 | Davidson |
| 7,710,825 B2 | 5/2010 | Betts et al. |
| 7,722,218 B2 | 5/2010 | Leung |
| 7,729,203 B2 | 6/2010 | Betts et al. |
| 7,755,974 B2 | 7/2010 | Betts et al. |
| 7,812,667 B2 | 10/2010 | Fagg |
| 7,870,496 B1 | 1/2011 | Sherwani |
| 7,890,867 B1 | 2/2011 | Margulis |
| 8,019,532 B2 | 9/2011 | Sheha et al. |
| 8,040,758 B1 | 10/2011 | Dickinson |
| 8,063,540 B2 | 11/2011 | Angelsen et al. |
| 8,082,100 B2 * | 12/2011 | Grace ................. G05D 1/02 701/1 |
| 8,364,806 B2 * | 1/2013 | Short ................... H04L 63/08 709/223 |
| 8,452,797 B1 | 5/2013 | Paleja et al. |
| 8,468,164 B1 | 6/2013 | Paleja et al. |
| 8,721,453 B2 | 5/2014 | Rosing |
| 9,439,411 B2 * | 9/2016 | Bailey ................. G08C 17/02 |
| 9,507,562 B2 | 11/2016 | Bailey |
| 9,572,335 B2 | 2/2017 | Bailey |
| 9,615,562 B2 | 4/2017 | Bailey |
| 2001/0054961 A1 | 12/2001 | Twining |
| 2002/0035574 A1 | 3/2002 | Dumas |
| 2002/0093541 A1 | 7/2002 | Schileru-Key |
| 2002/0099457 A1 | 7/2002 | Fredlund et al. |
| 2002/0116421 A1 | 8/2002 | Fox et al. |
| 2003/0046689 A1 * | 3/2003 | Gaos .................. G06Q 30/02 725/34 |
| 2003/0056419 A1 | 3/2003 | Squires et al. |
| 2003/0089020 A1 | 5/2003 | Dirito |
| 2003/0147981 A1 | 8/2003 | Gillam |
| 2004/0124297 A1 | 7/2004 | Steer |
| 2004/0162830 A1 * | 8/2004 | Shirwadkar ......... G06F 17/3087 |
| 2004/0193364 A1 | 9/2004 | Chojnacki |
| 2004/0249860 A1 | 12/2004 | Stechschulte et al. |
| 2005/0011105 A1 | 1/2005 | Cameron et al. |
| 2005/0037872 A1 | 2/2005 | Fredlund et al. |
| 2005/0102101 A1 | 5/2005 | Beesley et al. |
| 2006/0013066 A1 | 1/2006 | Nishimori et al. |
| 2006/0048434 A1 | 3/2006 | Congel |
| 2006/0119585 A1 | 6/2006 | Skinner |
| 2006/0224940 A1 | 10/2006 | Lee |
| 2006/0265931 A1 | 11/2006 | McFadden et al. |
| 2007/0011334 A1 | 1/2007 | Higgins et al. |
| 2007/0045010 A1 | 3/2007 | Kasperek |
| 2007/0058489 A1 | 3/2007 | Bratcher |
| 2007/0220798 A1 | 9/2007 | Davidson |
| 2008/0126935 A1 | 5/2008 | Blomgren |
| 2008/0165022 A1 | 7/2008 | Herz et al. |
| 2008/0204424 A1 | 8/2008 | Jin et al. |
| 2008/0246627 A1 | 10/2008 | Guazzelli |

(56) References Cited

U.S. PATENT DOCUMENTS

| | | |
|---|---|---|
| 2009/0064055 A1 | 3/2009 | Chaudhri et al. |
| 2009/0099871 A1 | 4/2009 | Gadodia |
| 2009/0105952 A1* | 4/2009 | Grace .................. G05D 1/0206 701/300 |
| 2009/0179789 A1 | 7/2009 | Haughay, Jr. et al. |
| 2009/0231190 A1 | 9/2009 | Grumbles |
| 2009/0240354 A1 | 9/2009 | Davidson |
| 2009/0241636 A1 | 10/2009 | Obori |
| 2009/0249247 A1 | 10/2009 | Tseng et al. |
| 2009/0258710 A1 | 10/2009 | Quatrochi |
| 2009/0271054 A1 | 10/2009 | Dokken |
| 2009/0287409 A1 | 11/2009 | Summers |
| 2009/0293336 A1 | 12/2009 | Lankinen |
| 2009/0295626 A1 | 12/2009 | Su |
| 2010/0049468 A1 | 2/2010 | Papadourakis |
| 2010/0080082 A1 | 4/2010 | Betts et al. |
| 2010/0121716 A1 | 5/2010 | Golan |
| 2010/0145601 A1 | 6/2010 | Kurtti et al. |
| 2010/0198650 A1 | 8/2010 | Shaw |
| 2010/0199225 A1 | 8/2010 | Coleman et al. |
| 2010/0226203 A1 | 9/2010 | Buttle et al. |
| 2010/0250122 A1 | 9/2010 | Kubota et al. |
| 2010/0295781 A1 | 11/2010 | Alameh et al. |
| 2010/0319235 A1 | 12/2010 | Panaro |
| 2011/0007035 A1 | 1/2011 | Shai |
| 2011/0013484 A1 | 1/2011 | Coleman et al. |
| 2011/0013485 A1 | 1/2011 | Maguire |
| 2011/0019887 A1 | 1/2011 | Roehrig et al. |
| 2011/0025720 A1 | 2/2011 | Jo et al. |
| 2011/0067290 A1 | 3/2011 | Miskatovic |
| 2011/0082644 A1 | 4/2011 | Imasaka et al. |
| 2011/0154183 A1 | 6/2011 | Burns et al. |
| 2011/0208479 A1 | 8/2011 | Chaves |
| 2011/0213515 A1 | 9/2011 | Haymart et al. |
| 2011/0214500 A1 | 9/2011 | Cabrera et al. |
| 2011/0257819 A1 | 10/2011 | Chen et al. |
| 2012/0001773 A1 | 1/2012 | Lyons et al. |
| 2012/0011437 A1 | 1/2012 | James et al. |
| 2012/0014220 A1 | 1/2012 | DePasqua |
| 2012/0047790 A1 | 3/2012 | Hess et al. |
| 2012/0069712 A1 | 3/2012 | Potanin et al. |
| 2012/0095978 A1 | 4/2012 | Levin et al. |
| 2012/0106300 A1 | 5/2012 | Maguire |
| 2012/0144384 A1 | 6/2012 | Baek |
| 2012/0144723 A1 | 6/2012 | Davidson |
| 2012/0185801 A1 | 7/2012 | Madonna et al. |
| 2012/0253485 A1 | 10/2012 | Weast et al. |
| 2012/0293323 A1 | 11/2012 | Kaib et al. |
| 2012/0316456 A1 | 12/2012 | Rahman et al. |
| 2012/0316458 A1 | 12/2012 | Rahman et al. |
| 2012/0317167 A1 | 12/2012 | Rahman et al. |
| 2013/0007665 A1 | 1/2013 | Chaudhri et al. |
| 2013/0040714 A1 | 2/2013 | Rosing |
| 2013/0074051 A1 | 3/2013 | Freeman |
| 2013/0096575 A1 | 4/2013 | Olson |
| 2013/0107031 A1 | 5/2013 | Atkinson |
| 2013/0271301 A1 | 10/2013 | Kabel et al. |
| 2013/0281087 A1* | 10/2013 | Ruhanen ........... H04L 29/12132 455/433 |
| 2013/0307720 A1 | 11/2013 | Lilburn |
| 2013/0343151 A1 | 12/2013 | Shiraki et al. |
| 2014/0012587 A1 | 1/2014 | Park |
| 2014/0032468 A1 | 1/2014 | Anandaraj |
| 2014/0071059 A1 | 3/2014 | Girault |
| 2014/0111368 A1 | 4/2014 | Lee et al. |
| 2014/0164375 A1 | 6/2014 | Persson et al. |
| 2014/0180566 A1 | 6/2014 | Malhotra |
| 2014/0195297 A1 | 7/2014 | Abuelsaad et al. |
| 2014/0358483 A1* | 12/2014 | da Rosa .................. A01K 97/00 702/188 |
| 2015/0019135 A1 | 1/2015 | Kacyvenski |
| 2015/0051786 A1 | 2/2015 | Wang |
| 2015/0054655 A1 | 2/2015 | Bailey |
| 2015/0054732 A1 | 2/2015 | Bailey |
| 2015/0054828 A1 | 2/2015 | Bailey |
| 2015/0054829 A1 | 2/2015 | Bailey |
| 2015/0055827 A1 | 2/2015 | Bailey |
| 2015/0055930 A1 | 2/2015 | Bailey |
| 2015/0057929 A1 | 2/2015 | Bailey |
| 2015/0057965 A1 | 2/2015 | Gaynor |
| 2015/0057968 A1 | 2/2015 | Bailey |
| 2015/0058020 A1 | 2/2015 | Bailey |
| 2015/0058237 A1 | 2/2015 | Bailey |
| 2015/0058323 A1 | 2/2015 | Bailey |
| 2015/0245777 A1 | 9/2015 | Della Torre et al. |
| 2015/0310524 A1 | 10/2015 | Gospodarek et al. |
| 2015/0313199 A1 | 11/2015 | Castaneda et al. |
| 2016/0095393 A1 | 4/2016 | Lin |
| 2016/0125348 A1 | 5/2016 | Dyer et al. |

FOREIGN PATENT DOCUMENTS

| | | |
|---|---|---|
| EP | 1 561 377 A1 | 8/2005 |
| EP | 1782687 | 5/2007 |
| EP | 2356902 A1 | 8/2011 |
| EP | 2 613 223 A1 | 7/2013 |
| GB | 2244195 A | 11/1991 |
| GB | 2426680 A | 12/2006 |
| GB | 2470904 | 12/2010 |
| JP | 2004 207812 A | 7/2004 |
| JP | 2006-158239 A | 6/2006 |
| JP | 2010 193284 A | 9/2010 |
| JP | 2011 139647 A | 7/2011 |
| WO | 1998/02037 A1 | 1/1998 |
| WO | 2004/088572 | 10/2004 |
| WO | 2010/056392 | 5/2010 |
| WO | WO 2012/059734 A1 | 5/2012 |
| WO | 2012/170163 | 12/2012 |
| WO | 2014088508 A1 | 6/2014 |
| ZA | 2003-08052 A | 7/2004 |

OTHER PUBLICATIONS

PCT International Search Report and Written Opinion; PCT/IB2014/063980; dated Jan. 5, 2015.
PCT International Search Report and Written Opinion; PCT/IB2014/063982; dated Dec. 22, 2014.
PCT International Search Report and Written Opinion; PCT/IB2014/063975; dated Dec. 3, 2014.
PCT International Search Report and Written Opinion; PCT/IB2014/063974; dated Dec. 2, 2014.
Allen, et al.; Upper Extremity Kinematic Trends of Fly-Casting; Establishing the Effects of Line Length; Sports Biomechanics; vol. 7, No. 1; Jan. 1, 2008; pp. 38-53.
First look at new Mio Link ANT +/Bluetooth Smart optical heart rate wrist band; http://www.dcrainmaker.com/2014/01/mio-link-first-look.html; Jan. 6, 2014 (accessed Apr. 18, 2016).
SAS, "SAS BI Dashboard 4.31 User's Guide", Second Edition, by SAS Electronic book, Aug. 1, 2012, downloaded at http://support.sas.com/documentation/cdl/en/bidbrdug/ 65580/PDF/default/bidrdrug.pdf.
PCT International Search Report and Written Opinion; PCT/IB2013/060285, dated Feb. 18, 2014; all enclosed pages cited.
PCT International Search Report and Written Opinion; PCT/IB2014/063976, dated Dec. 12, 2014; all enclosed pages cited.
PCT International Search Report and Written Opinion; PCT/IB2014/063983, dated Mar. 5, 2015; all enclosed pages cited.
PCT International Search Report and Written Opinion; PCT/US2013/047645, dated Sep. 27, 2013; all enclosed pages cited.
PCT International Search Report and Written Opinion; PCT/US2013/047869, dated Oct. 21, 2013; all enclosed pages cited.
PCT International Search Report and Written Opinion; PCT/US2013/047926, dated Oct. 11, 2013; all enclosed pages cited.
PCT International Search Report and Written Opinion; PCT/US2013/048129, dated Oct. 17, 2013; all enclosed pages cited.
PCT International Search Report and Written Opinion; PCT/US2013/048177, dated Oct. 21, 2013; all enclosed pages cited.
PCT International Search Report and Written Opinion; PCT/IB2014/063973, dated Nov. 28, 2014; all enclosed pages cited.

(56) References Cited

OTHER PUBLICATIONS

PCT International Search Report and Written Opinion; PCT/IB2014/063981, dated Feb. 10, 2015; all enclosed pages cited.
PCT International Search Report and Written Opinion; PCT/IB2014/063978, dated Dec. 19, 2014; all enclosed pages cited.
PCT International Search Report and Written Opinion; PCT/IB2014/063977, dated Nov. 28, 2014; all enclosed pages cited.
McElderry; At-Sea Observing Using Video-Based Electronic Monitoring; Prepared for: Electronic Monitoring Workshop Jul. 29-30, 2008; Archipelago Marine Research Ltd.
Office Action Issued in Canadian Patent Application 2,921,317, dated Feb. 7, 2017.
Cristando et al. "Nikeplus Ecosystem Strategy" retreived Sep. 1, 2017 from <http://studylib.net/doc/8718940/nikeplus-ecosystem-strategy> 12 pages.
Joey Davidson, "Jaybird Reign Review—Lightweight, simple, lacking" Feb. 28, 2016, Technobuffalo, retrieved Sep. 1, 2017 from <https://www.technobuffalo.com/reviews/jaybird-reign-review/> 14 pages.

* cited by examiner

FISHING DATA SHARING AND DISPLAY

CROSS-REFERENCE TO RELATED APPLICATIONS

This application claims the benefit of U.S. Provisional Patent Application Ser. No. 61/868,444, filed Aug. 21, 2013 and titled FISHING DATA COLLECTION AND USE, the disclosure of which is incorporated herein by reference.

BACKGROUND

Discussion of the Related Art

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Recreational and competitive fishing as a sport is growing in popularity. Fishermen engaged in these activities can record and share results manually. Typically, fishermen engaged in competitive fishing record results by hand, and then compare the recorded results to determine ranking.

SUMMARY

Various implementations described herein are directed to viewing shared fishing data, and sharing fishing data, including, for example, the rate at which fishing casts were made over time, the location at which fishing casts or catches occurred, or the number of fish caught, can be useful for a fisherman and can increase a fisherman's enjoyment of the sport. By reviewing shared fishing data before, during, and after a fishing trip, a fisherman can track fishing performance over time and analyze performance in certain conditions. Sharing fishing data can also allow a fisherman to compare personal fishing data with fishing data recorded by other fishermen. A cloud software service may be used to collect, store, share, and display fishing data to subscribers (i.e., users). The cloud software service may allow subscribers to share different fishing data with different subscribers. For example, only a subscriber's friends may be given permission to view the subscriber's location data from a fishing trip, while all subscribers may be able to view the total number of fish that the subscriber caught during the fishing trip.

Various implementations described herein are directed to determining a plurality of actions for granting permissions to subscribers to access fishing data. In one implementation, a non-transitory computer-readable medium having stored thereon computer-executable instructions which, when executed by a computer, cause the computer to perform various actions. The actions may include automatically receiving fishing data recorded during a fishing trip. The action may include receiving a selection of a first group of subscribers that can access the fishing data. The actions may also include granting permissions to the first group of subscribers to access the fishing data.

Various implementations described herein are directed to displaying fishing data to a subscriber. In one implementation, a non-transitory computer-readable medium having stored thereon computer-executable instructions which, when executed by a computer, cause the computer to perform various actions. The actions may include receiving data corresponding to a subscriber. The actions may include receiving fishing data from multiple fishermen, wherein the fishing data had been automatically recorded during one or more fishing trips. The actions may include selecting at least a portion of the fishing data. The actions may also include displaying at least the portion of the fishing data to the subscriber.

Various implementations described herein are directed to a method of storing fishing data. The method may include receiving fishing data automatically recorded during a fishing trip. The method may include determining one or more subscribers that can access the fishing data. The method may also include granting permissions to the subscribers to access the fishing data.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

Figure 1A:
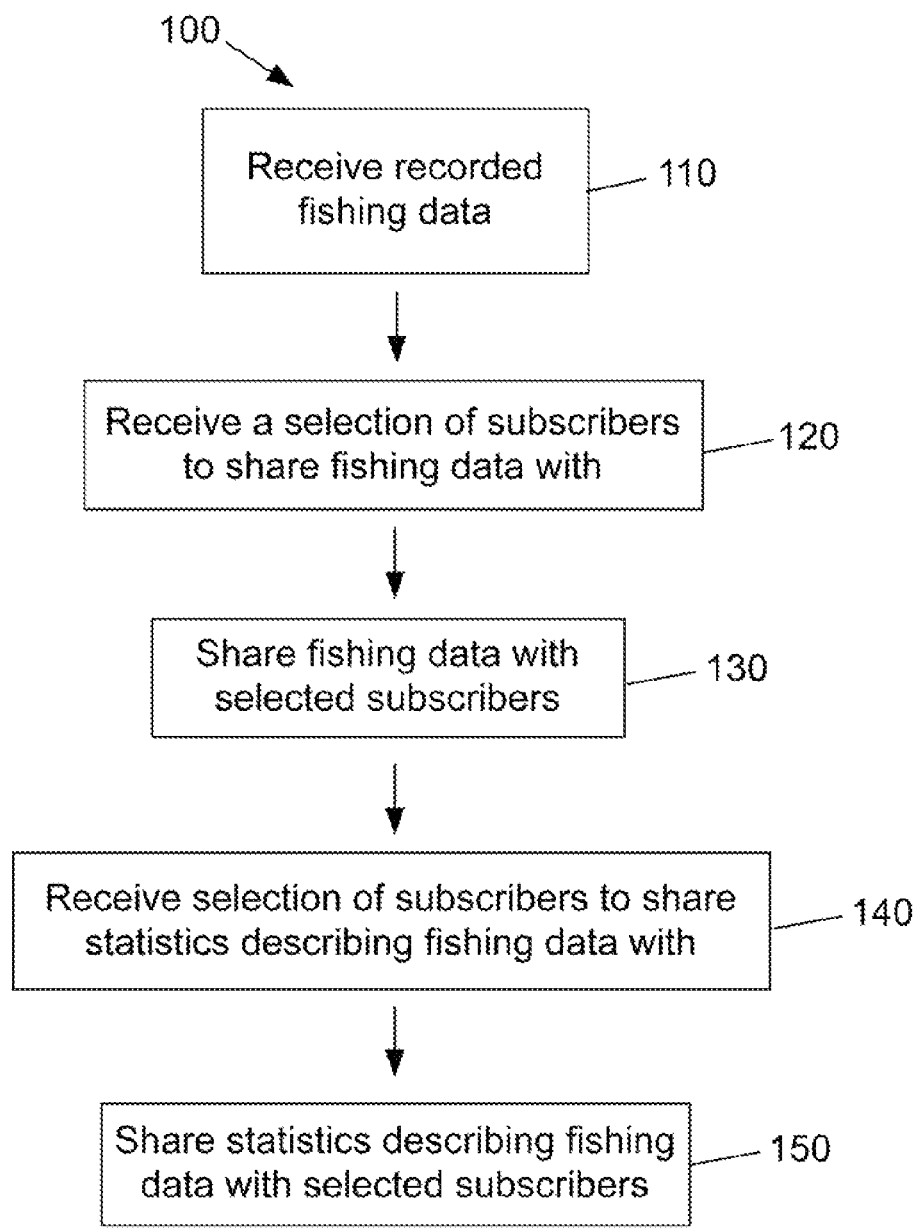
FIG. 1A illustrates a flow diagram of a method for sharing fishing data in accordance with various implementations described herein.

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Figure 1B:
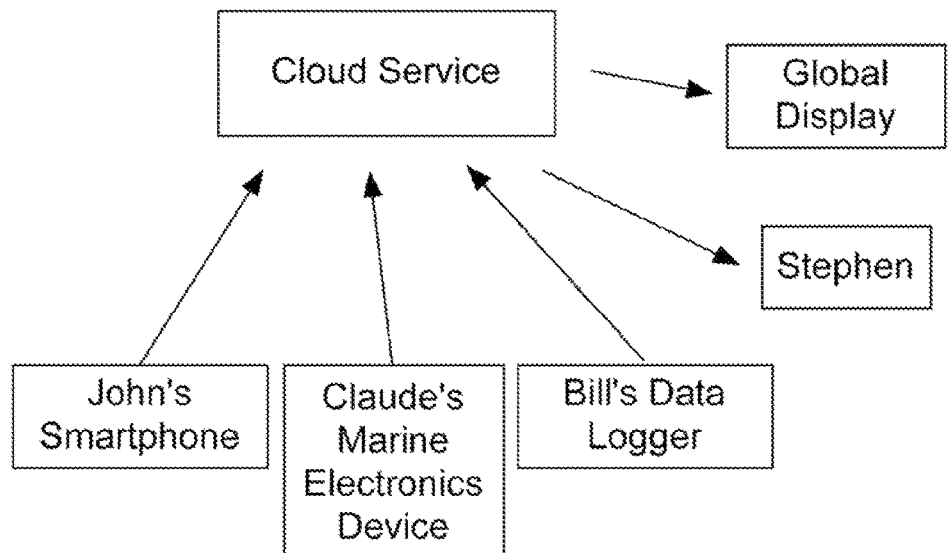
FIG. 1B illustrates sharing fishing data using a cloud service in accordance with various implementations described herein.

Various implementations of fishing data sharing and display described herein will now be described in more detail with reference to FIGS. 1-10. FIG. 1A illustrates a flow diagram of a method 100 for sharing fishing data in accordance with various implementations described herein. FIG. 1B illustrates sharing fishing data using a cloud service in accordance with various implementations described herein. In one implementation, method 100 may be performed by any computing device, such as computer system 900 (described in FIG. 9), a marine electronics device 800 (described in FIG. 8), a smart phone, a cloud software service, or any other computerized device. It should be understood that while method 100 indicates a particular order of execution of operations, in some implementations, certain portions of the operations may be executed in a different order. Further, in some implementations, additional operations or steps may be added to method 100. Likewise, some operations or steps may be omitted. Additionally, the operations may be executed on more than one computerized device.

As mentioned above, the computer system 900 may be loaded with a set of instructions (software) to perform method 100. At block 110, the software may receive recorded fishing data. The fishing data may have been automatically recorded during a fishing trip by a wearable device, a marine electronics device, a smartphone, or combinations thereof. For example, a wearable device may detect motion corresponding to a cast and automatically record that a cast has occurred and the time of the cast. The fishing data may be automatically received by the software. For example, during a fishing trip, a wearable device may transmit data to the software automatically after detecting a cast. The sources used to collect fishing data, and the types of fishing data collected by the different sources are further explained with reference to FIG. 10.

FIG. 1B is an example of recorded fishing data being received by a cloud service. In FIG. 1B, recorded fishing data is being received from three subscribers. Recorded fishing data is being transmitted from John's smartphone, Claude's marine electronics device, and Bill's data logger to the cloud service. The transmissions may occur during the subscribers' fishing trips, or after.

At block 120, the software may receive a selection of subscribers to share the received fishing data with. This selection may be in any format, such as usernames for subscribers of a cloud system, email addresses, names, or any other format. The selection may be made using a fishing data sharing selection user interface, described further in FIG. 2. Using a fishing data sharing selection interface, a subscriber may select one or more subscribers to share data with, or a group of subscribers to share data with, and the subscriber may select the data to share with those subscribers or groups. For example, a subscriber may select a group of fishermen to share data with, and the subscriber may select to share the weather and number of bites recorded during a fishing trip with that group.

In one implementation, a subscriber on a cloud service may select friends or groups to share received fishing data with every time new fishing data is received by the service.

For example, in FIG. 1A, John may have selected Stephen as a friend using the cloud service. Then, data received by the cloud service from John may always be shared with Stephen.

At block 130, the software may share fishing data with selected subscribers. In one implementation, the software may transmit the fishing data to the selected subscribers. In another implementation, the fishing data may be stored and the subscribers may be given access to the stored data. For example, the data may be stored in a database, and the subscribers may be given permission to access the database. In a third implementation, a cloud service may control access to fishing data, and the cloud service may grant the selected subscribers access to the fishing data. In FIG. 1B, the cloud service is sharing fishing data collected from John, Claude, and Bill with Stephen. Stephen may then view the fishing data by accessing the cloud service, or the shared fishing data may be transmitted to Stephen.

The fishing data shared at block 130 may include all of the received data, or may be a subset of the received data. For example, the shared data may be the received data with location information removed. In one implementation, the location data may be shared in a less precise format. For example, instead of providing the specific location on a lake, the location shared may be the name of the lake.

At block 140, the software may receive a second selection of subscribers with which to share statistics describing the received fishing data. For example, if the fishing data contained information regarding each cast, the statistics to be shared with the second selection of subscribers may be the total number of casts, the rate at which casts were made, a count of the type of casts, or other statistics describing the fishing data. The statistics may include the total number of bites, catches, casts, averages or ratios of fishing data, or any other statistics describing the fishing data.

At block 150, the software may share the statistics with the second selection of subscribers. The software may grant the second selection of subscribers permission to access the statistics. The statistics may be generated using the data received at block 110. The subscribers selected at block 120 may receive more data than the subscribers selected at block 140. For example, the subscribers at block 120 may be close friends who are granted access to all of the data recorded during a fishing trip, while the subscribers at block 140 may be a much larger group of subscribers who are only able to view the total number of fish caught during the trip. In FIG. 1B, statistics describing the fishing data received from John, Claude, and Bill are shared with a global set of subscribers. For example, all subscribers may be able to view the total number of casts that John, Claude, and Bill made.

In one implementation, fishing data may be captured during a fishing trip and uploaded to a cloud software service in real time. This may allow subscribers to remotely monitor a fisherman's data throughout a fishing trip. Additionally, the location of a fisherman may be uploaded throughout a fishing trip, which may be used to monitor the location of a fisherman for safety reasons.

Figure 2:
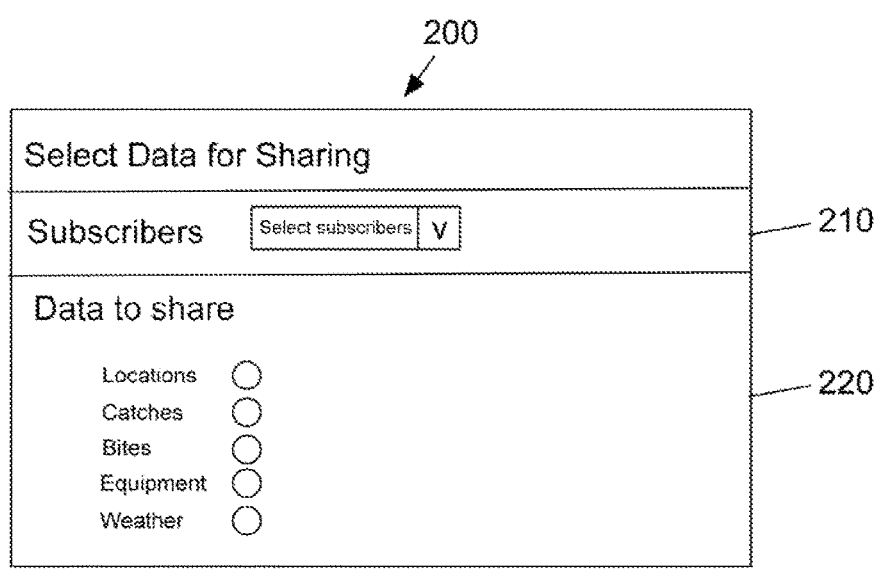
FIG. 2 illustrates a fishing data sharing selection interface in accordance with various implementations described herein.

FIG. 2 illustrates a fishing data sharing selection user interface in accordance with various implementations described herein. In one implementation, the selection interface window 200 may be displayed before or after a subscriber transmits fishing data to a cloud software service. The interface window 200 may also be shown whenever a subscriber requests to share fishing data. At field 210, the interface window 200 may allow a selection of one or more subscribers or groups of subscribers. The selected subscribers or groups are to be given access to shared fishing data.

At field 220, the interface window 200 allows a subscriber to select fishing data to share. Although field 220 displays a list of fishing data categories for sharing, the interface window 200 may allow a subscriber to select any type of fishing data. In one implementation, the interface window 200 may allow a subscriber to select all fishing data recorded during a single fishing trip. In another implementation, the interface window 200 may allow a subscriber to select all fishing data recorded in a particular location. The interface window 200 may be implemented in any fashion that allows a subscriber to select data for sharing and select subscribers or groups to receive the shared data.

Figure 3:
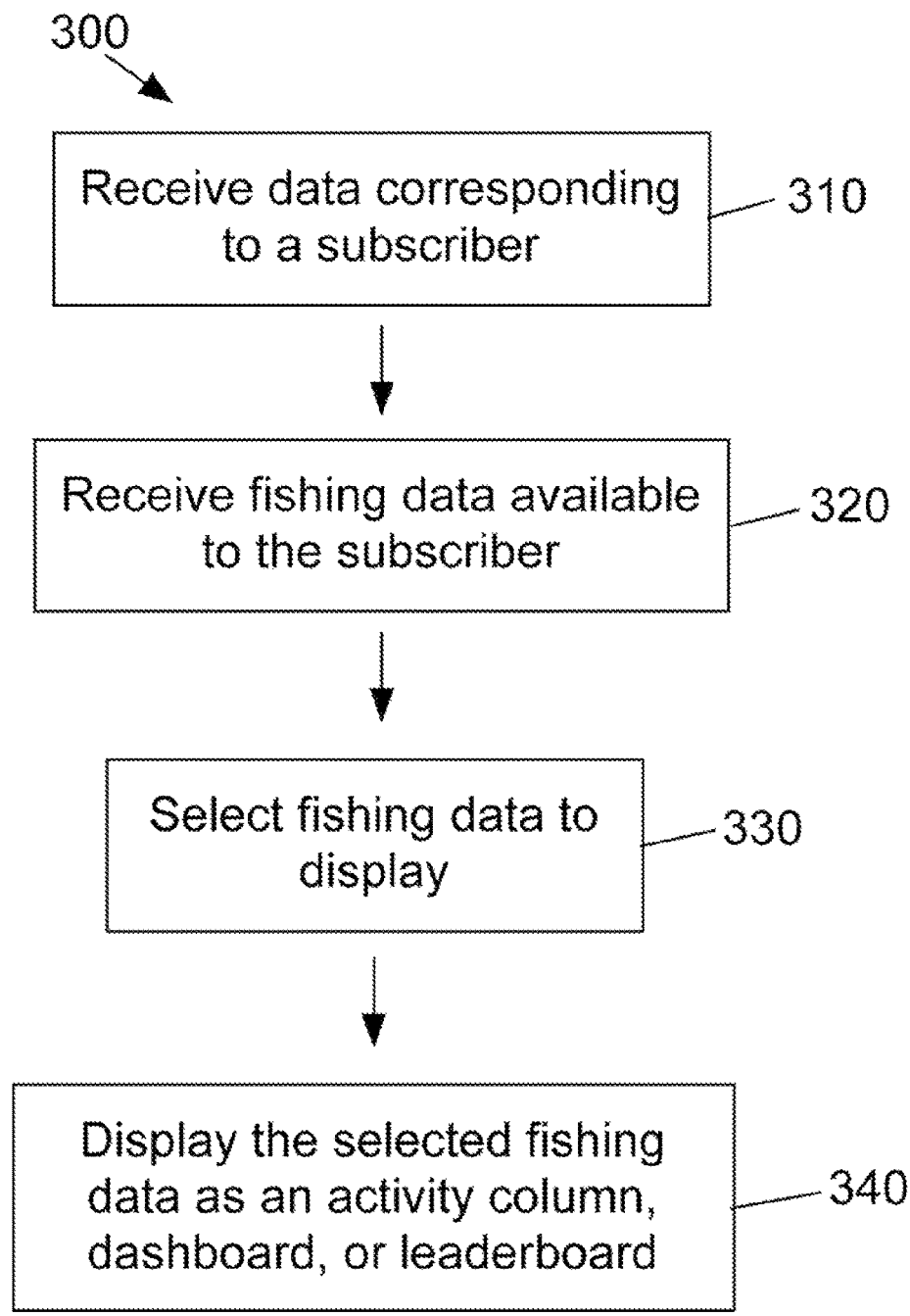
FIG. 3 illustrates a flow diagram of a method for displaying fishing data in accordance with various implementations described herein.

FIG. 3 illustrates a flow diagram of a method 300 for displaying fishing data in accordance with various implementations described herein. In one implementation, method 300 may be performed by any computing device, such as computer system 900 (described in FIG. 9), a marine electronics device 800 (described in FIG. 8), a smart phone, a cloud software service, or any other computerized device. It should be understood that while method 300 indicates a particular order of execution of operations, in some implementations, certain portions of the operations may be executed in a different order. Further, in some implementations, additional operations or steps may be added to method 300. Likewise, some operations or steps may be omitted. Additionally, the operations may be executed on more than one computerized device.

As mentioned above, the computer system 900 may be loaded with a set of instructions (software) to perform method 300. At block 310, the software may receive data corresponding to a subscriber. The data may be a username, login, email address, name, or any other information used to identify a subscriber.

At block 320, the software may receive fishing data available to the subscriber. The fishing data may have been recorded by multiple fishermen. The fishing data may have been automatically recorded during a fishing trip. For example, the software may receive fishing data recorded by the subscriber. In another example, the software may receive fishing data recorded by a friend of the subscriber, where the friend has granted permission for the subscriber to access the data. The fishing data may be data shared using method 100. For example, in FIG. 1B, the fishing data may be the data shared by John, Claude, and Bill. The software may then use method 300 to display the shared fishing data to Stephen. In one implementation, at block 320, the software may receive the fishing data by accessing the fishing data stored in a database.

At block 330, the software may select a portion of the fishing data received at block 320 to display. The software may select a portion of the fishing data received at block 320, or all of the fishing data received at block 320. The received fishing data may be fishing data, statistics describing the fishing data, or both. The fishing data may be selected using any criteria. In one implementation, the data may be selected based on how recent the data is. In another implementation, the data may be selected based on how relevant the data will be to a subscriber. In a third implementation, the selected data may be all data shared with a subscriber. In a fourth implementation, the selected data may be all data shared or captured within a requested time period. In a fifth implementation, the selected data may be selected based on the preferences of a subscriber. For example, if a subscriber prefers viewing data captured near a specific location, only data captured near that location would be selected.

Figure 4:
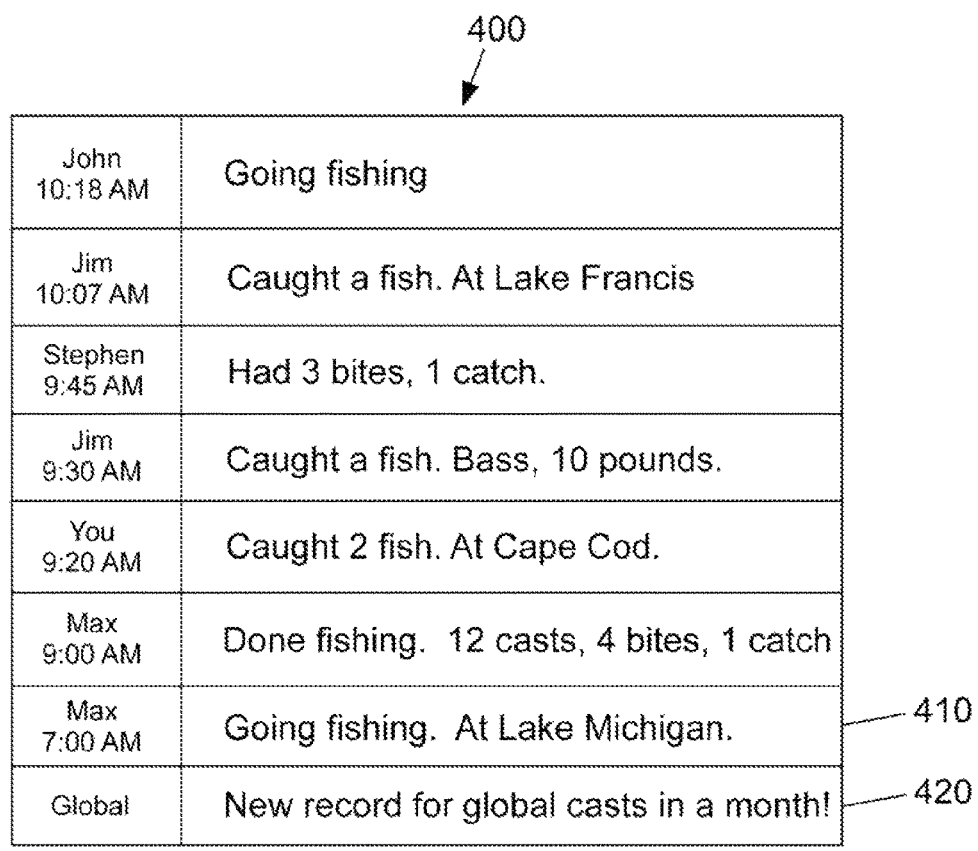
FIG. 4 illustrates a fishing data activity column display in accordance with various implementations described herein.
Figure 5:
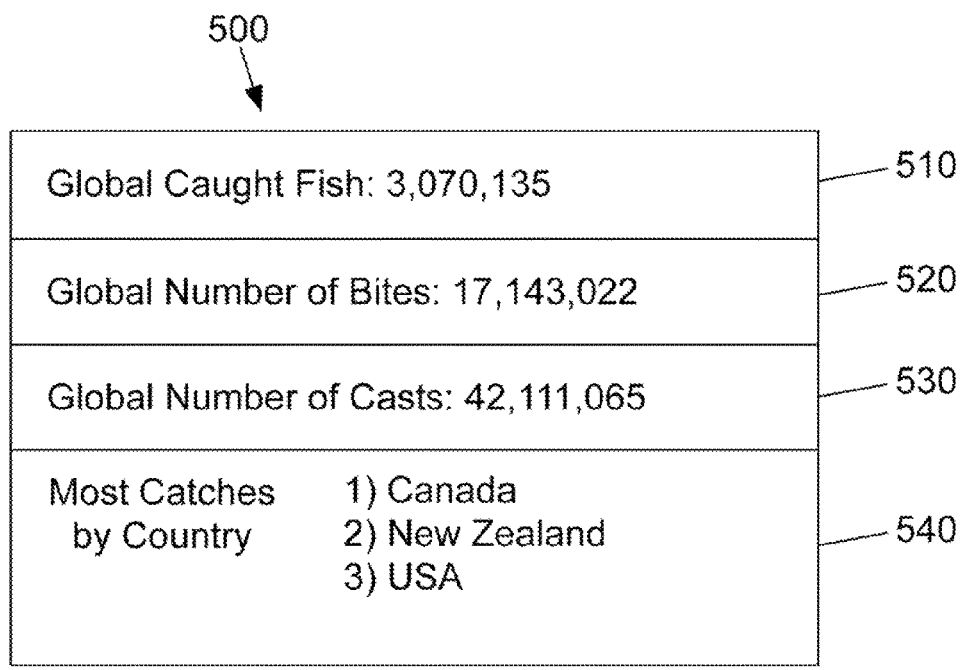
FIG. 5 illustrates a global fishing data dashboard display in accordance with various implementations described herein.
Figure 6:
FIG. 6 illustrates a leaderboard fishing data display in accordance with various implementations described herein.

At block 340, the software may display the selected fishing data as an activity column display 400 as illustrated in FIG. 4, a dashboard display 500 as illustrated in FIG. 5, or a leaderboard display 600 as illustrated in FIG. 6.

FIG. 4 illustrates an activity column fishing data display in accordance with implementations of various techniques described herein. The fishing data displays illustrated in FIGS. 4-6 may be displayed on a marine electronics device as described in FIG. 8, a computer system as described in FIG. 9, a wearable electronics device as described in FIG. 7, a smartphone device, or any other display device. The displays illustrated in FIGS. 4-6 may be generated by a cloud software service.

In the illustrated display 400, fishing data describing the fishing trips of a number of different fishermen are displayed in an activity column format. For example, in FIG. 1B, Stephen may view the data shared by John, Claude, and Bill using an activity column. John, Claude, and Bill may share data automatically with Stephen using the cloud service by selecting Stephen as a friend. In one implementation, a subscriber may access a cloud service using a web browser, and an activity column may be displayed.

Although the data is displayed as sorted by time, it may be sorted by any variable, for example popularity, or relevance to the viewer. The activity column 400 may include any relevant information regarding fishing, such as the beginning or ending of a fishing trip, the occurrence of a fishing event such as a cast, bite, or catch, the location of an event, the time of an event, pictures, videos, or any other relevant fishing data. For example, at event 410, the fishing data display includes information describing the beginning of a fishing trip for the subscriber Max, and the location of Max's fishing trip, which is Lake Michigan.

An activity column 400 may also display information regarding maintenance of marine equipment. For example, an activity column 400 may display a reminder to perform regular maintenance on a marine engine, or may provide an alert that a piece of marine equipment appears to be failing.

At event 420, the activity column 400 may display global information, such as the occurrence of a new global record. This may be information regarding all subscribers who submit data to the fishing service, or a subset of subscribers, for example all of the fisherman in one country. An activity column 400 may also include information about upcoming events or competitions.

FIG. 5 illustrates a global fishing data dashboard display in accordance with various implementations described herein. In one implementation, a global fishing data dashboard display may display fishing statistics collected by all subscribers of a cloud service. Although, global fishing data dashboard display 500 is illustrated as displaying global data, a fishing data dashboard may display fishing data or statistics describing fishing data collected from any number of fishermen. At 510, 520, and 530, the global fishing data display 500 shows a global number of caught fish, bites, and casts. At 540, global fishing data display shows a list of countries in which the most catches have occurred.

Although the global fishing data dashboard display 500 is illustrated as showing a number of catches, bites, and casts, the display 500 may display any relevant fishing data, such as the number of different types of fish caught, the weight of caught fish, the length of time spent fishing, ratios of fishing data, or any other relevant information or statistics. Additionally, the global fishing data dashboard display 500 may display statistics describing all collected fishing data, or any subset of subscribers or data.

In one implementation, the global fishing data dashboard display 500 may show information regarding an individual fisherman. As such, the dashboard display 500 may show total fishing statistics for this one fisherman only. For example, the display 500 may show the total number of catches, or any other fishing statistic or data describing the performance of this one fisherman.

FIG. 6 illustrates a leaderboard fishing data display in accordance with various implementations described herein. Leaderboard display 600 may display the results of a fishing competition or a list of ranked subscribers. In FIG. 6, a list of subscribers are ranked by the number of caught fish. A leaderboard display 600 may contain subscribers ranked by any criteria, such as catches, casts, bites, number of different types of fish caught, weight of caught fish, length of time spent fishing, or based on any other fishing data.

In one implementation, a fishing competition may be created using a cloud software service. The fishing competition may be for a selected group of fishermen, or may be open to all subscribers of the cloud software service. Results of the fishing competition may be displayed using a leaderboard display 600. A fishing competition may be based on any fishing data, and extend for any period of time. A fishing competition may be bound to a specific location or area.

Wearable Electronic Device

Figure 7:
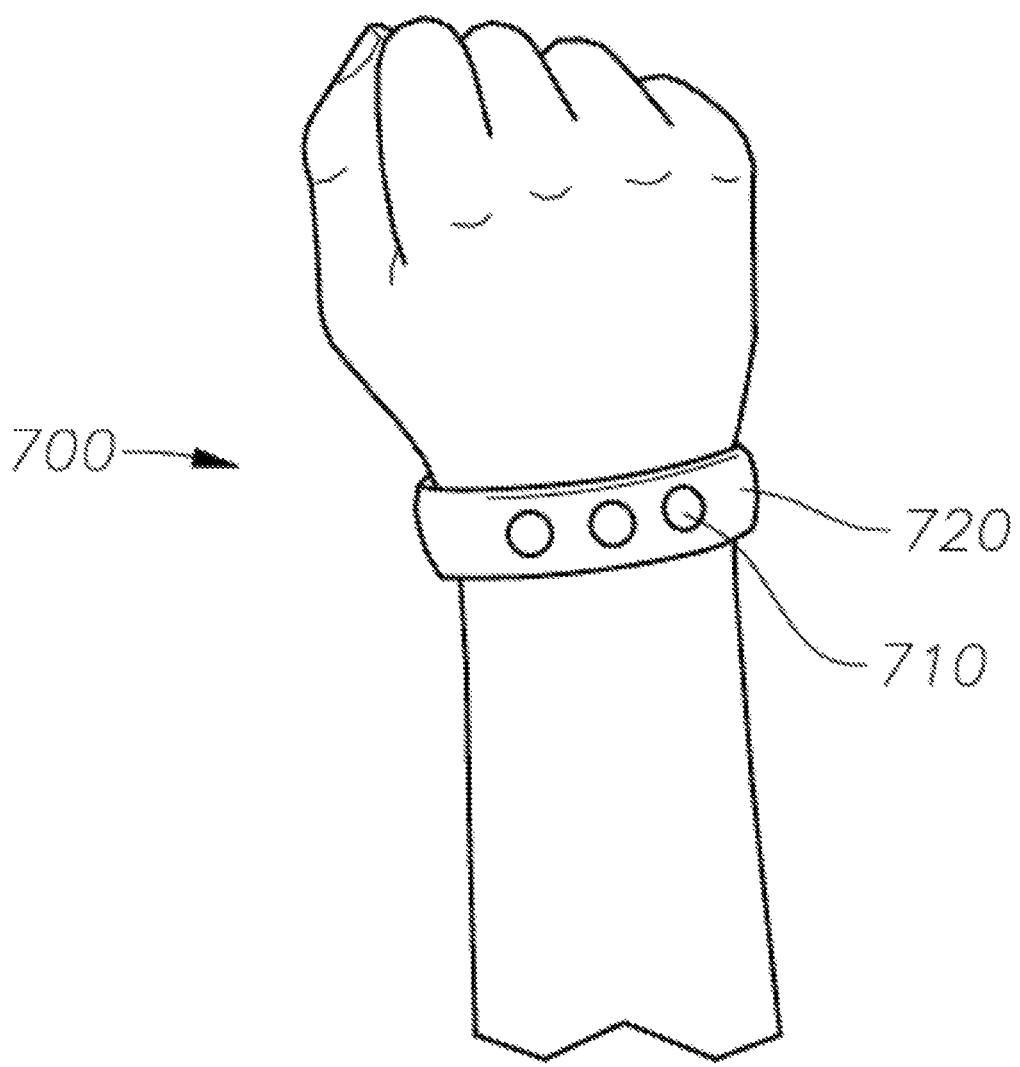
FIG. 7 illustrates a wearable electronic device used to record fishing data in accordance with various implementations described herein.

FIG. 7 illustrates a wearable electronic device 700 used to record fishing data in accordance with various implementations described herein. The wearable electronic device 700 may be worn around a fisherman's arm or wrist. The wearable electronic device 700 may also be attached to a fishing rod. The wearable electronic device 700 may include a housing 720. The housing 720 may be in the shape of a band. The housing 720 may be made of a combination of plastics and rubbers, or of any other synthetic material.

The wearable electronic device 700 may include one or more buttons 710. The one or more buttons 710 may be used for user input, such as to indicate the occurrence of a bite or catch, or to input the length and weight of a caught fish. The wearable electronic device 700 may contain a computer 900 and motion sensors or other sensors. Using the sensors, wearable electronic device 700 may automatically record fishing data during a fishing trip. For instance, the wearable electronic device 700 may automatically count casts, determine the type of cast used, determine the occurrence of a bite or catch, determine the weight and length of a caught fish, the number of caught fish, or other fishing data. In one implementation, the wearable electronic device 700 may automatically record the occurrence of a cast and the type of cast, whereas the occurrence of a bite, the occurrence of a catch, and the weight of a caught fish may be entered using the buttons 710. The fishing data may then be recorded in memory. The fishing data may be displayed in an activity column as illustrated in FIG. 4, a dashboard as illustrated in FIG. 5, or a leaderboard as illustrated in FIG. 6. The fishing data may be shared using the method described in FIG. 1A, or displayed using the method described in FIG. 3. The wearable electronic device 700 may contain wireless technology, such as Bluetooth or Wi-Fi, to transmit recorded data to a marine electronics device 800, a smart phone, a cloud software service, or any other computer system 900.

Marine Electronics Device

Figure 8:
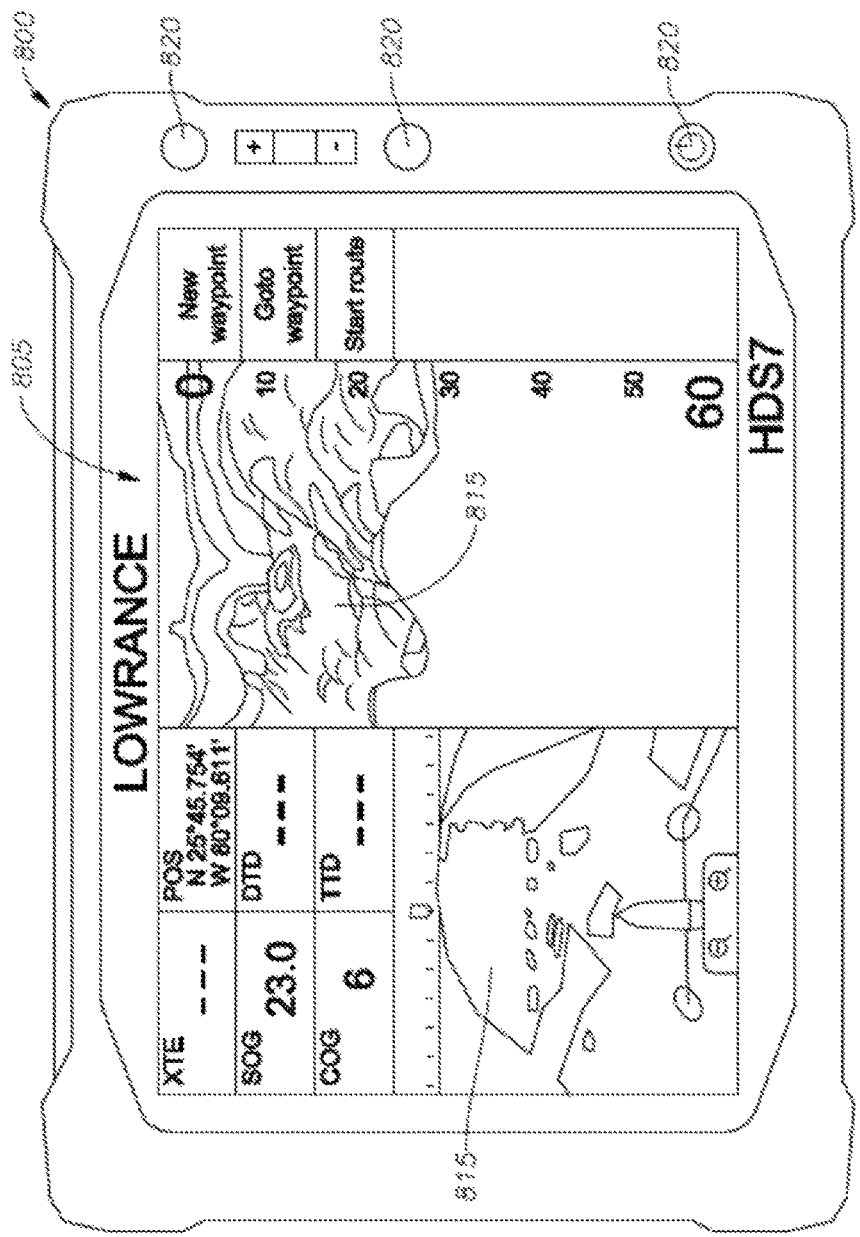
FIG. 8 illustrates a schematic of a marine electronics device in accordance with implementations of various techniques described herein.

FIG. 8 illustrates a schematic diagram of a marine electronics device 800 in accordance with various implementations described herein. The marine electronics device 800 includes a screen 805. In certain implementations, the screen 805 may be sensitive to touching by a finger. In other implementations, the screen 805 may be sensitive to the body heat from the finger, a stylus, or responsive to a mouse. The marine electronics device 800 may display marine electronic data 815. The marine electronic data types 815 may include chart data, radar data, sonar data, steering data, dashboard data, navigation data, fishing data displays as illustrated in FIGS. 4-6, and the like. The marine electronics device 800 may also display the user interface for a cloud software service. The marine electronics device 800 may include a plurality of buttons 820, which may be either physical buttons or virtual buttons, or a combination thereof. The marine electronics device may contain a computer system 900, which is described in more detail in FIG. 9.

The marine electronics device 800 may contain a positioning system or receive positioning system coordinates from an attached device, such as a Bluetooth global positioning system (GPS) receiver. The marine electronics device 800 may also receive fishing data from sensors contained within or attached to the marine electronics device 800, or from another device transmitting fishing data to the marine electronics device, such as a wearable electronic device 700. The marine electronics device 800 may process the positioning system coordinates and the collected or received fishing data throughout a fishing trip, and then transmit the data to a cloud software service. The fishing data may be shared using the method described in FIG. 1A, or displayed using the method described in FIG. 3.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may also be implemented in distributed computing environments, including a cloud computing environment, where tasks are performed by remote processing devices that are linked through a communications network, e.g., by hardwired links, wireless links, or combinations thereof. In a distributed computing environment, program modules may be located in both local and remote computer storage media including memory storage devices.

Figure 9:
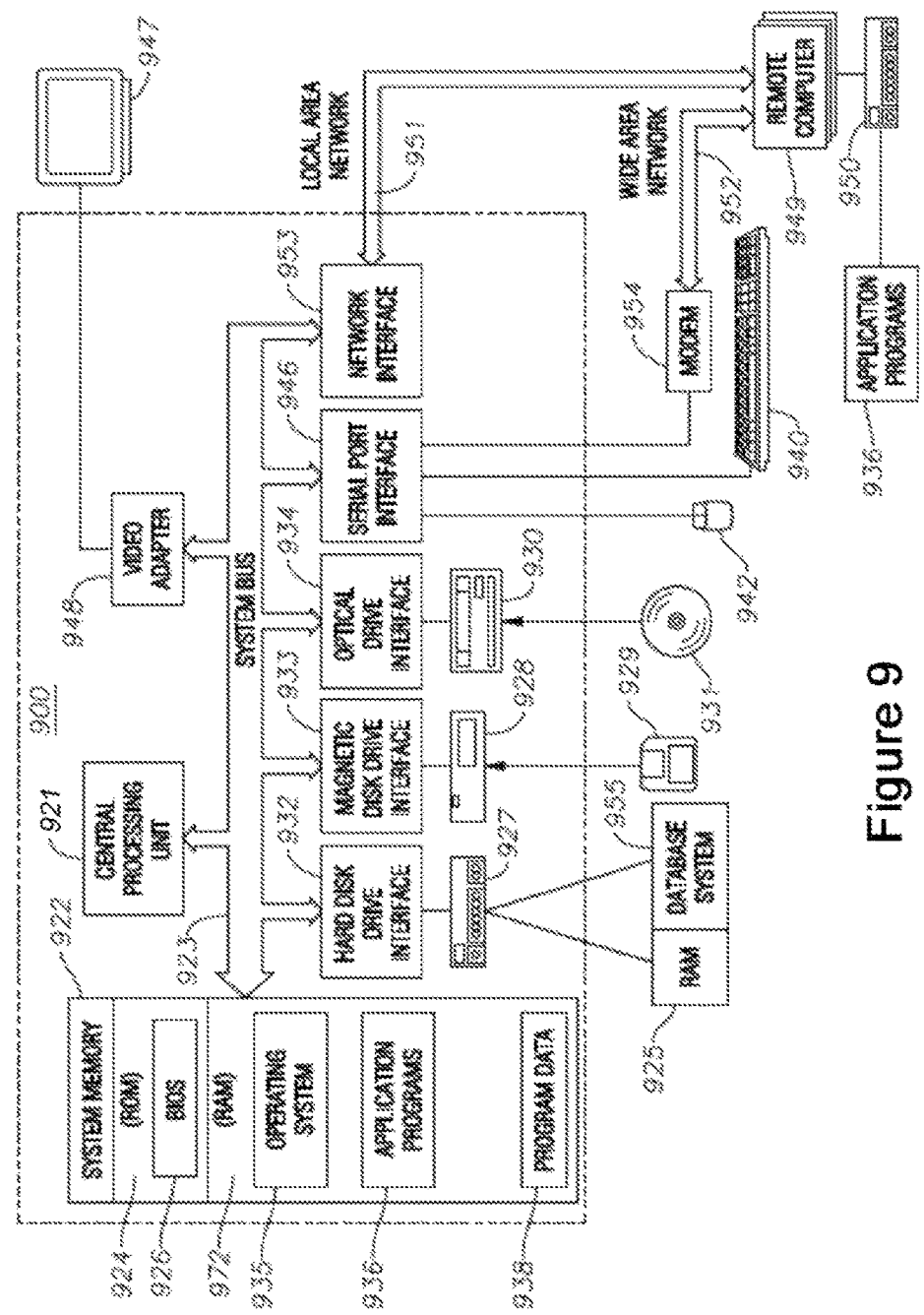
FIG. 9 illustrates a schematic diagram of a computing system in which the various technologies described herein may be incorporated and practiced.

FIG. 9 illustrates a computer system 900 into which implementations of various technologies and techniques described herein may be implemented. Computing system 900 may be a conventional desktop, a handheld device, a wearable electronic device, a controller, a personal digital assistant, a server computer, an electronic device/instrument, a laptop, a tablet, part of a marine electronics system, or part of a cloud computing system. It should be noted, however, that other computer system configurations may be used.

The computing system 900 may include a central processing unit (CPU) 921, a system memory 922 and a system bus 923 that couples various system components including the system memory 922 to the CPU 921. Although only one CPU is illustrated in FIG. 9, it should be understood that in some implementations the computing system 900 may include more than one CPU. The system bus 923 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 922 may include a read only memory (ROM) 924 and a random access memory (RAM) 925. A basic input/output system (BIOS) 926, containing the basic routines that help transfer information between elements within the computing system 900, such as during start-up, may be stored in the ROM 924. The computing system may be implemented using a printed circuit board containing various components including processing units, data storage memory, and connectors.

The computing system 900 may further include a hard disk drive 927 for reading from and writing to a hard disk, a magnetic disk drive 928 for reading from and writing to a removable magnetic disk 929, and an optical disk drive 930 for reading from and writing to a removable optical disk 931, such as a CD ROM or other optical media. The hard disk drive 927, the magnetic disk drive 928, and the optical disk drive 930 may be connected to the system bus 923 by a hard disk drive interface 932, a magnetic disk drive interface 933, and an optical drive interface 934, respectively. The drives and their associated computer-readable media may provide nonvolatile storage of computer-readable instructions, data structures, program modules and other data for the computing system 900.

Although the computing system 900 is described herein as having a hard disk, a removable magnetic disk 929 and a removable optical disk 931, it should be appreciated by those skilled in the art that the computing system 900 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system 900. Communication media may embody computer readable instructions, data structures, program modules or other data in a modulated data signal, such as a carrier wave or other transport mechanism and may include any information delivery media. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on the hard disk 927, magnetic disk 929, optical disk 931, ROM 924 or RAM 925, including an operating system 935, one or more application programs 936, program data 938, and a database system 955. The one or more application programs 936 may contain program instructions configured to perform methods 100 and 300 according to various implementations described herein. The operating system 935 may be any suitable operating system that may control the operation of a networked personal or server computer, such as Windows® XP, Mac OS® X, Unix-variants (e.g., Linux® and BSD®), and the like.

A user may enter commands and information into the computing system 900 through input devices such as a keyboard 940 and pointing device 942. Other input devices may include a microphone, joystick, game pad, satellite dish, scanner, user input button, or the like. These and other input devices may be connected to the CPU 921 through a serial port interface 946 coupled to system bus 923, but may be connected by other interfaces, such as a parallel port, game port or a universal serial bus (USB). A monitor 947 or other type of display device may also be connected to system bus 923 via an interface, such as a video adapter 948. The monitor 947 may be used to display fishing data displays as described in FIGS. 4-6 and a fishing data selection interface as described in FIG. 2. In addition to the monitor 947, the computing system 900 may further include other peripheral output devices such as speakers and printers.

Further, the computing system 900 may operate in a networked environment using logical connections to one or more remote computers 949. The logical connections may be any connection that is commonplace in offices, enterprise-wide computer networks, intranets, and the Internet, such as local area network (LAN) 951 and a wide area network (WAN) 952. The remote computers 949 may each include application programs 936 similar to that as described above. The computing system 900 may use a Bluetooth radio to wirelessly communicate with another device.

When using a LAN networking environment, the computing system 900 may be connected to the local network 951 through a network interface or adapter 953. When used in a WAN networking environment, the computing system 900 may include a modem 954, wireless router or other means for establishing communication over a wide area network 952, such as the Internet. The modem 954, which may be internal or external, may be connected to the system bus 923 via the serial port interface 946. In a networked environment, program modules depicted relative to the computing system 900, or portions thereof, may be stored in a remote memory storage device 950. It will be appreciated that the network connections shown are exemplary and other means of establishing a communications link between the computers may be used.

Fishing Data Collection

Figure 10:
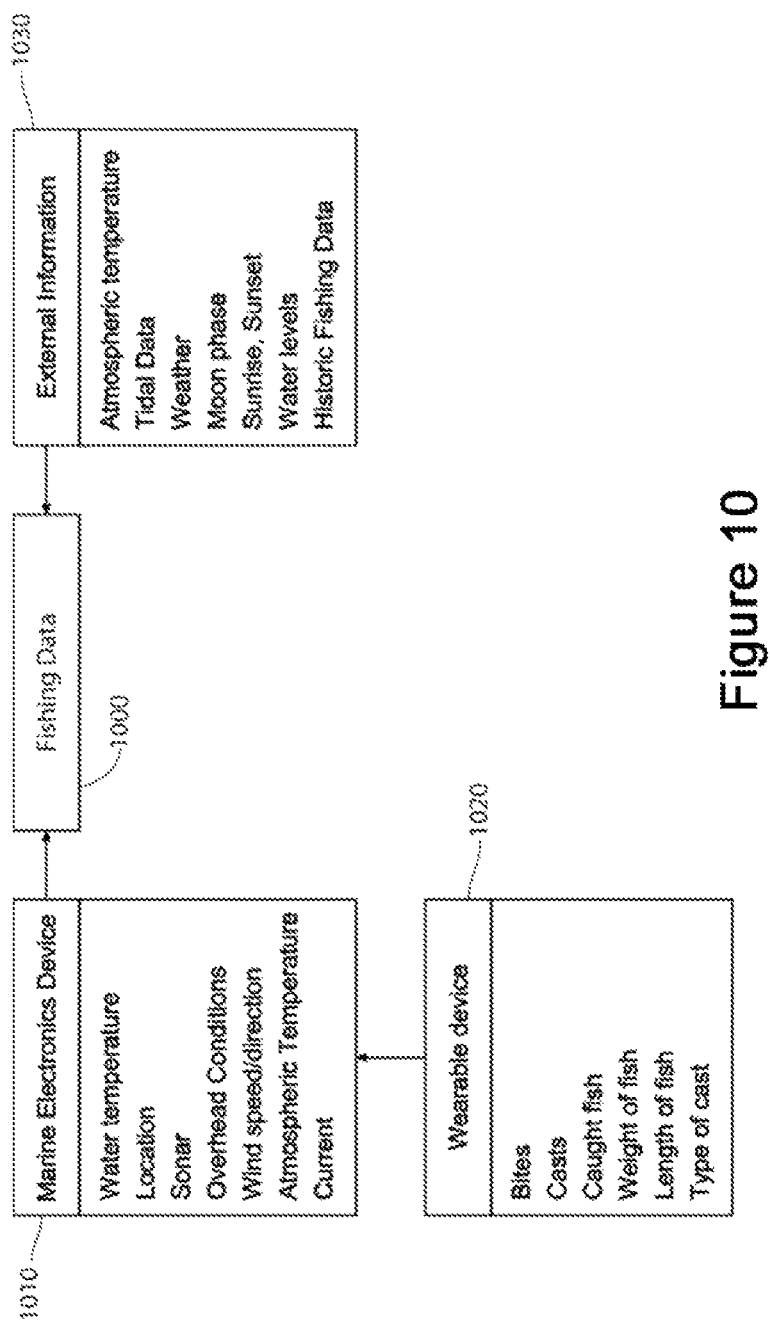
FIG. 10 illustrates a diagram of data sources used to collect fishing data in accordance with various implementations described herein.

FIG. 10 illustrates a diagram of data sources used to collect fishing data 1000 in accordance with implementations of various techniques described herein. The fishing data 1000 may include bites, casts, caught fish, the weight of a caught fish, the length of a caught fish, the type of cast, or averages, ratios and rates of fishing data. For example, fishing data 1000 may include the rate of casts made over time, the average number of casts made per hour, or the ratio of bites to caught fish. The fishing data 1000 may be collected on a computer system 900, a marine electronics device 800, a smart phone, a cloud software service, or on any device capable of collecting fishing data 1000. This fishing data 1000 may be displayed using any of the fishing data displays described in FIGS. 4-6. The fishing data may be shared using method 100, described in FIG. 1A, and displayed using method 300, described in FIG. 3.

Wearable electronic device 1020, described in further detail in FIG. 7, may record fishing data 1000 such as bites, casts, caught fish, the weight of a caught fish, the length of a caught fish, the type of cast, and other fishing data. The fishing data 1000 recorded using the wearable electronic device 1020 may be transmitted to a marine electronics device 1010, a smart phone, a cloud software service, or any other device. The marine electronics device 1010 is described in more detail with reference to FIG. 8. Although fishing data 1000 is described as being recorded by the wearable electronic device 1020, it may also be recorded by any other electronic device capable of automatically recording fishing data.

The marine electronics device 1010, described in further detail in FIG. 8, may record fishing data 1000 such as water temperature, location, sonar, overhead conditions, wind speed and direction, atmospheric temperature, current, and other fishing data. This information may be transmitted to a computer system 900, another marine electronics device 800, a smart phone, a cloud software service, or to any device capable of collecting fishing data 1000.

External information 1030 may also be retrieved and stored as fishing data 1000. The external information 1030 may be retrieved from the Internet or any other source. The external information 1030 may be retrieved by or transmitted to a computer system 900, marine electronics device 800, a smart phone, a cloud software service, or any device capable of collecting fishing data 1000. The external information 1030 may be transmitted in the form of a database or any other format to a system collecting fishing data 1000. The external information 1030 may include atmospheric temperature, tidal data, weather, moon phase, sunrise, sunset, water levels, historic fishing data, and other fishing data.

While the foregoing is directed to implementations of various techniques described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A non-transitory computer-readable medium having stored thereon computer-executable instructions which, when executed by a computer, cause the computer to:

automatically receive, via wireless transmission from a wearable electronic device comprising a motion sensor, fishing data corresponding to one or more fishing statistics recorded during a fishing trip in a marine vessel on a body of water, wherein the one or more fishing statistics comprise at least one of cast information, bite information, or catch information, and wherein the fishing data is detected by the motion sensor of the wearable electronic device, wherein the wearable electronic device and the motion sensor are not directly connected to a fishing line;

determine one or more locations traveled by the marine vessel associated with the fishing data such that each of the one or more fishing statistics is associated with at least one location;

receive a selection of a first group of subscribers that can access the fishing data, wherein each subscriber in the first group of subscribers is identified in the selection by a username;

grant permissions to the first group of subscribers to access the fishing data; and transmit the fishing data to at least one of the subscribers in the first group of subscribers based on the permissions.

2. The non-transitory computer-readable medium of claim 1, wherein the instructions further cause the computer to:
select a set of fishing data from the received fishing data; and
display the selected set of fishing data as an activity column, a dashboard, or a leaderboard.

3. The non-transitory computer-readable medium of claim 1, wherein the fishing data is automatically recorded in memory by the wearable electronic device or a marine electronics device.

4. The non-transitory computer-readable medium of claim 1, wherein the fishing data is received during a fishing trip.

5. The non-transitory computer-readable medium of claim 1, wherein the fishing data comprises a number of casts, number of bites, a number of catches, the weight of a caught fish, the length of a caught fish, a type of cast, or combinations thereof.

6. The non-transitory computer-readable medium of claim 1, wherein the fishing data comprises water temperature, location data, sonar data, overhead conditions, wind speed, wind direction, atmospheric temperature, current data, or combinations thereof.

7. The non-transitory computer-readable medium of claim 1, wherein the fishing data comprises atmospheric temperature, tidal data, weather, moon phase, sunrise, sunset, water levels, historic fishing data, or combinations thereof.

8. The non-transitory computer-readable medium of claim 1, wherein the instructions further cause the computer to:
receive a selection of a second group of subscribers with whom statistics describing the fishing data can be shared; and
grant permissions to the second group of subscribers to access the statistics describing the fishing data.

9. The non-transitory computer-readable medium of claim 8, wherein the statistics comprise an average or total number of casts, an average or total number of catches, an average or total number of bites, an average or total weight of caught fish, an average or total length of caught fish, or combinations thereof.

10. The non-transitory computer-readable medium of claim 1, wherein the instructions that cause the computer to grant permissions to the first group of subscribers to access the fishing data comprises instructions that cause the computer to allow the first group of subscribers to access the received fishing data in a database.

11. A non-transitory computer-readable medium having stored thereon computer-executable instructions which, when executed by a computer, cause the computer to:
receive data corresponding to a subscriber;
receive fishing data from multiple fishermen, wherein the fishing data corresponds to one or more fishing statistics wirelessly received from a one or more wearable electronic devices and is automatically recorded during one or more fishing trips in one or more marine vessels, wherein the one or more fishing statistics comprise at least one of cast information, bite information, or catch information for each fisherman, wherein each of the casts is detected by a motion sensor of a wearable electronic device, wherein the wearable electronic device and the motion sensor are not directly connected to a fishing line;

receive location information corresponding to one or more locations traveled by the one or more marine vessels associated with the fishing data, wherein each of the one or more fishing statistics is associated with at least one location;

receive a selection of at least a portion of the fishing data; and transmit the at least the portion of the fishing data to display the at least the portion of the fishing data.

12. The non-transitory computer-readable medium of claim 11, wherein the instructions that cause the computer to receive the fishing data from multiple fisherman comprises instructions that cause the computer to access fishing data stored in a database.

13. The non-transitory computer-readable medium of claim 11, wherein the fishing data is automatically recorded in memory by the one or more wearable electronic devices, one or more marine electronics devices, one or more smartphones, or combinations thereof.

14. The non-transitory computer-readable medium of claim 11, wherein the at least the portion of the fishing data comprises an average or total number of casts, an average or total number of catches, an average or total number of bites, an average or total weight of caught fish, an average or total length of caught fish, or combinations thereof.

15. The non-transitory computer-readable medium of claim 11, wherein the instructions that cause the computer to select at least the portion of the fishing data comprises instructions that cause the computer to select the portion of the fishing data based on a requested time period.

16. The non-transitory computer-readable medium of claim 11, wherein the instructions that cause the computer to select at least a portion of the fishing data comprises instructions that cause the computer to select the portion of the fishing data based on the preferences of the subscriber.

17. The non-transitory computer-readable medium of claim 11, wherein the instructions that cause the computer to display the at least a portion of the fishing data comprises instructions that cause the computer to display the at least the portion of the fishing data chronologically.

18. The non-transitory computer-readable medium of claim 11, wherein the data corresponding to the subscriber is a username or login.

19. A method for storing fishing data, comprising:
detecting, by a motion sensor of a wearable electronic device, fishing data corresponding to one or more fishing statistics recorded during a fishing trip in a marine vessel on a body of water, wherein the one or more fishing statistics comprise at least one of cast information, bite information, or catch information, wherein the wearable electronic device and the motion sensor are not directly connected to a fishing line;

determining one or more locations traveled by the marine vessel associated with the fishing data such that each or the one or more fishing statistics is associated with at least one location;

recording the fishing data on the wearable electronic device;

wirelessly transmitting the fishing data by the wearable electronic device;

receiving, via the wireless transmission of the wearable electronic device, fishing data automatically recorded during fishing trip;

determining one or more subscribers that can access the fishing data; and granting permissions to the subscribers to access the fishing data.

20. The method of claim 19, wherein the fishing data is automatically recorded in memory by the wearable electronic device, a smartphone, a marine electronics device, or combinations thereof.

* * * * *